United States Patent [19]
Zinnen

[11] Patent Number: 5,019,271
[45] Date of Patent: * May 28, 1991

[54] EXTRACTIVE CHROMATOGRAPHIC SEPARATION PROCESS FOR RECOVERING 3,5-DIETHYLTOLUENE

[75] Inventor: Hermann A. Zinnen, Evanston, Ill.

[73] Assignee: UOP, Des Plaines, Ill.

[*] Notice: The portion of the term of this patent subsequent to Jul. 10, 2007 has been disclaimed.

[21] Appl. No.: 443,800

[22] Filed: Nov. 28, 1989

Related U.S. Application Data

[63] Continuation of Ser. No. 292,184, Dec. 30, 1988, abandoned.

[51] Int. Cl.$^5$ .............................................. B01D 15/08
[52] U.S. Cl. .................................... 210/656; 210/674; 210/198.2; 208/310 Z; 585/828
[58] Field of Search .................. 585/828; 208/310 Z; 216/656, 670, 674, 198.2

[56] References Cited

U.S. PATENT DOCUMENTS

| | | | |
|---|---|---|---|
| 2,985,589 | 5/1961 | Broughton et al. | 210/34 |
| 3,040,777 | 6/1962 | Carson et al. | 137/625.15 |
| 3,422,848 | 1/1969 | Liebman et al. | 137/625.15 |
| 3,699,182 | 10/1972 | Cattanach | 208/310 Z |
| 3,706,812 | 12/1972 | De Rosset et al. | 260/674 SA |
| 3,864,416 | 2/1975 | Campbell | 585/828 |
| 3,878,129 | 4/1975 | Rosback | 585/828 |
| 3,894,109 | 7/1975 | Rosback | 585/828 |
| 3,943,184 | 3/1976 | Rosback | 585/828 |
| 4,041,192 | 9/1977 | Neuzil | 585/828 |
| 4,159,284 | 6/1979 | Seko et al. | 585/478 |
| 4,402,832 | 9/1983 | Gerhold | 210/659 |
| 4,423,279 | 12/1983 | Kulprathipanja | 585/828 |
| 4,467,126 | 8/1984 | Zinnen | 210/670 |
| 4,471,114 | 9/1984 | Sherman et al. | 536/127 |
| 4,482,777 | 11/1984 | Neuzil | 585/828 |
| 4,584,424 | 4/1986 | Barthomeuf | 208/310 Z |
| 4,642,397 | 2/1987 | Zinnen | 210/670 |
| 4,717,778 | 1/1988 | Zinnen | 585/828 |
| 4,940,548 | 7/1990 | Zinnen | 210/656 |

FOREIGN PATENT DOCUMENTS

| | | | |
|---|---|---|---|
| 5148620 | 4/1976 | Japan | 585/828 |
| 557216 | 1/1980 | Japan | 585/828 |

*Primary Examiner*—Ernest G. Therkorn
*Attorney, Agent, or Firm*—Thomas K. McBride; John F. Spears, Jr.; Jack H. Hall

[57] ABSTRACT

This invention comprises a process for separating 3,5-diethyltoluene from a feed mixture comprising 3,5-diethyltoluene and at least one isomer thereof, which process comprises contacting the mixture at adsorption conditions with an adsorbent comprising an X zeolite cation exchange with a K cation, thereby selectively adsorbing the 3,5-diethyltoluene. The remainder of the feed mixture is removed by desorption at desorption conditions with a desorbent material comprising a monocyclic alkyl-substituted aromatic hydrocation, e.g., p- or m-diethylbenzene or p-cymene and optionally, a diluent, e.g., isooctane.

6 Claims, 2 Drawing Sheets

EXTRACTIVE CHROMATOGRAPHIC SEPARATION PROCESS FOR RECOVERING 3,5-DIETHYLTOLUENE

BACKGROUND OF THE INVENTION

This is a continuation of copending application Ser. No. 292,184 filed on Dec. 30, 1988, now abandoned.

1. FIELD OF THE INVENTION

The field of art to which this invention pertains is the solid bed adsorptive separation of isomeric mixtures. More specifically, the invention relates to a process for separating isomers of diethyltoluenes (DET), and particularly, 3,5-diethyltoluene from the other diethyltoluene isomers by employing a solid bed adsorption system.

2. BACKGROUND INFORMATION

The 3,5-diethyltoluene isomer is an important starting material for making diethyltoluene diamine, from which polyureas and polyurethanes are derived Also, 3,5-diethyltoluene finds application as a desorbent material in certain adsorptive chromatographic separations, e.g., p-xylene from its isomers.

It is well known in the separation art that certain crystalline aluminosilicates can be used to separate hydrocarbon types from mixtures thereof. Furthermore, X and Y zeolites have been employed in a number of processes to separate individual hydrocarbon isomers. However, no adsorptive chromatographic separation processes have come to light for separating diethyltoluene isomers.

It is, however, known that crystalline aluminosilicates, or zeolites, used in other adsorptive separations of various mixtures, can be in the form of agglomerates having high physical strength and attrition resistance. Methods for forming the crystalline powders into such agglomerates include the addition of an inorganic binder, generally a clay comprising a silicon dioxide and aluminum oxide, to the high purity zeolite powder in wet mixture. The blended clay zeolite mixture is extruded into cylindrical type pellets or formed into beads which are subsequently calcined in order to convert the clay to an amorphous binder of considerable mechanical strength As binders, clays of the kaolin type, water permeable organic polymers or silica are generally used.

The invention herein can be practiced in fixed or moving adsorbent bed systems, but the preferred system for this separation is a countercurrent simulated moving bed system, such as described in Broughton U.S. Pat. No. 2,985,589, incorporated herein by reference Cyclic advancement of the input and output streams can be accomplished by a manifolding system, which are also known, e.g., by rotary disc valves shown in U.S. Pat. Nos. 3,040,777 and 3,422,848. Equipment utilizing these principles are familiar, in sizes ranging from pilot plant scale (deRossett U.S. Pat. No. 3,706,812) to commercial scale in flow rates from a few ml per hour to many thousands of gallons per hour The invention may also be practiced in a cocurrent, pulsed batch or continuous process, like those described in U.S. Pat. Nos. 4,159,284 and 4,402,832, respectively.

The functions and properties of adsorbents and desorbents in the chromatographic separation of liquid components are well-known, but for reference thereto, Zinnen et al U.S. Pat. No. 4,642,397 is incorporated herein.

Although numerous uses for isomers of DET or mixtures thereof are known, e.g., as precursors of reactants, e.g., curing agents or isocyanates for making polyurethanes, e.g., diethyltoluene diamine and diethyltoluene diisocyanate, they have recently been found to be a highly advantageous "heavy desorbent" for a chromatographic process for separating para-xylene from mixtures of xylene isomers as disclosed in Zinnen application Ser. No. 197,740, filed May 23, 1988, now U.S. Pat. No. 4,864,069 DET isomers are preferred especially for separating xylene mixtures which also contain $C_9$ aromatics, the latter of which are difficult to separate from p-diethylbenzene, a frequently used desorbent in commercial p-xylene separation processes, e.g., the Parex process of the assignee, UOP.

Currently, mixtures of DET isomers are used in the preparation of polyurethane precursors, but it would be highly desirable to make the precursors from highly pure individual isomers of DET in order to obtain higher yields of the desired reactant. Additionally, the yield of 3,5-DET can be increased by isomerizing, at isomerization conditions, the raffinate isomer mixture with an isomerization catalyst, for example, zeolites containing trace metals, as is known in the art, and recycling the raffinate with increased 3,5-DET concentration with the feed to the instant process.

SUMMARY OF THE INVENTION

In brief summary, the invention is a chromatographic process for separating 3,5-diethyltoluene from a mixture comprising 3,5-diethyltoluene and at least one isomer thereof. The process comprises contacting the DET isomer mixture at adsorption conditions with an adsorbent comprising an X-type zeolite, cation exchanged with a potassium cation thereby selectively adsorbing the 3,5-diethyltoluene thereon. The remainder of the feed mixture is then removed, i.e., eluted, from the adsorbent and the 3,5-diethyltoluene is recovered by desorption at desorption conditions with a desorbent material comprising monocyclic alkyl-substituted aromatics, e.g., p- or m-diethylbenzene or p-cymene.

Other embodiments of our invention encompass details about feed mixtures, adsorbents, desorbent materials and operating conditions, all of which are hereinafter disclosed in the following discussion of each of the facets of the present invention.

DETAILED DESCRIPTION OF THE INVENTION

Figure 1:
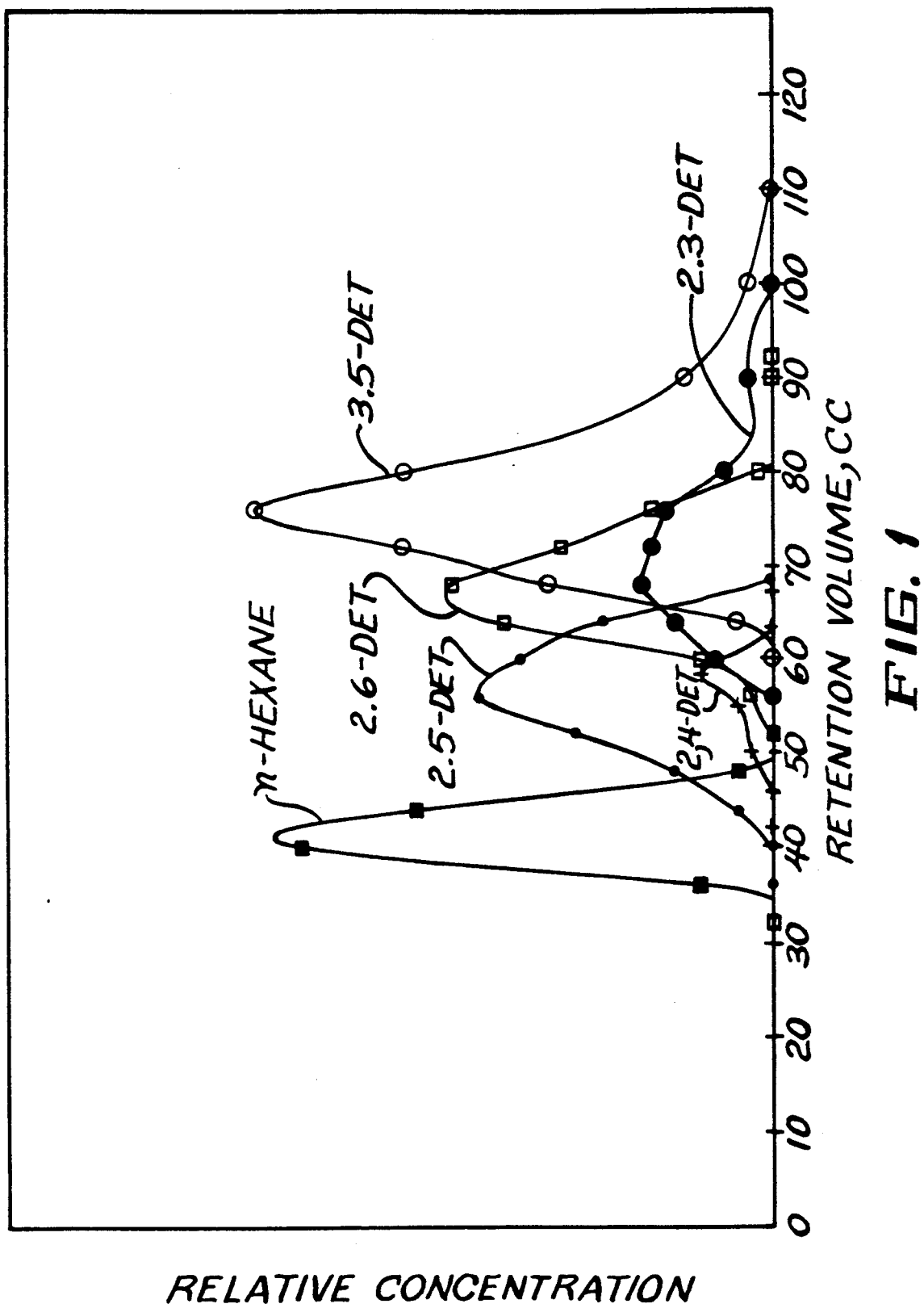
FIG. 1 is a chromatograph trace of the separation of 3,5-diethyltoluene from a mixture of DET isomers with KX zeolite adsorbent and a desorbent comprising 30% p-diethylbenzene and 70% isoctane.

Adsorbents to be used in the process of this invention comprise specific crystalline aluminosilicates or molecular sieves, namely, X zeolites. The zeolites have known cage structures in which the alumna and silica tetrahedra are intimately connected in an open three-dimensional network to form cage-like structures with window-like pores. The tetrahedra are cross-linked by the sharing of oxygen atoms with spaces between the tetrahedra occupied by water molecules prior to partial or total dehydration of this zeolite. The dehydration of the zeolite results in crystals interlaced with cells having molecular dimensions and thus, the crystalline aluminosilicates are often referred to as "molecular sieves" when the separation which they effect is dependent essentially upon differences between the sizes of the feed molecules as, for instance, when smaller normal paraffin molecules are separated from larger isoparaffin molecules by using a particular molecular sieve. In the process of this invention, however, the term "molecular sieves", although widely used, is not strictly suitable since the separation of specific aromatic isomers is apparently dependent on differences in electrochemical attraction between the different isomers and the adsorbent rather than on pure physical size differences between the isomer molecules.

In hydrated form, the crystalline aluminosilicates encompass type X zeolites which are represented by Formula 1 below in terms of moles of oxides:

Formula 1

$$(0.9\pm0.2)M_{2/n}O:Al_2O_3:(2.5\pm0.5)SiO_2:yH_2O$$

where "M" is a cation having a valence of not more than 3 which balances the electrovalence of the tetrahedra and is generally referred to as an exchangeable cation, "n" represents the valence of the cation, and "y", which represents the moles of water, is a value up to about 9 depending upon the identity of "M" and the degree of hydration of the crystal. As noted from Formula 1, the $SiO_2/Al_2O_3$ mole ratio is $2.5\pm0.5$. As the X zeolite is initially prepared, the cation "M" is usually predominantly sodium, that is, the major cation at the exchangeable cationic sites is sodium and the zeolite is therefore referred to as a sodium-X zeolite. Depending upon the purity of the reactants used to make the zeolite, other cations mentioned above may be present, however, as impurities. In the present invention, the cation "M" is partially or completely exchanged by potassium ions.

Typically, adsorbents used in separative processes contain the crystalline material dispersed in an amorphous matrix or binder, having channels and cavities therein which enable liquid access to the crystalline material. Silica, alumna, clay or mixtures thereof are inorganic substances typical of such matrix materials. Organic materials, such as polymers of styrene/divinylbenzene, are also used as a matrix. The binder aids in forming or agglomerating the crystalline particles which otherwise would comprise a fine powder. The adsorbent may thus be in the form of particles such as extrudates, aggregates, tablets, macrospheres or granules having a desired particle range, preferably from about 16 to about 60 mesh (Standard U.S. Mesh) (1.9 mm to 250 micron).

Feed mixtures which can be utilized in the process of this invention will comprise 3,5-DET and at least one other $C_{11}$ aromatic isomer. Crude hydrocarbon streams containing substantial quantities of $C_{11}$ aromatic isomers are produced by alkylation and isomerization processes, which are well known to the refining and petrochemical arts.

To separate the 3,5-DET from a feed mixture containing 3,5-DET and at least one other $C_{11}$ aromatic, the mixture is contacted with the adsorbent at adsorption conditions and the 3,5-DET is more selectively adsorbed and retained by the adsorbent while the other components are relatively unadsorbed and are eluted from the interstitial void spaces between the particles of adsorbent and from the surface of the adsorbent. The adsorbent containing the more selectively adsorbed isomer is referred to as a "rich" adsorbent. The 3,5-DET is then recovered from the rich adsorbent by contacting the rich adsorbent with a desorbent material at desorption conditions. As aforementioned, the raffinate containing the relatively non-adsorbed isomers of DET can be isomerized to increase the concentration of the 3,5-DET isomer and recycled to the separation process to increase the recovery of 3,5-DET.

In this process, which employs a potassium-exchanged zeolite as the adsorbent and which is generally operated continuously at substantially constant pressures and temperatures to ensure liquid phase, the desorbent material relied upon must be judiciously selected to satisfy several criteria. First, the desorbent material should displace an extract component from the adsorbent with reasonable mass flow rates without itself being so strongly adsorbed as to unduly prevent the extract component from displacing the desorbent material in a following adsorption cycle. Secondly, the desorbent material must be compatible with the particular adsorbent and the particular feed mixture. More specifically, it must not reduce or destroy the critical selectivity of the adsorbent for an extract component with respect to the raffinate component or react chemically with the feed components. The desorbent material should additionally be easily separable from the feed mixture that is passed into the process. Both the raffinate components and the extract components are typically removed from the adsorbent in admixture with desorbent material, and without a method of separating at least a portion of desorbent material, the purity of the extract product and the raffinate product would not be very high nor would the desorbent material be available for reuse in the process. It is, therefore, contemplated that any desorbent material used in this process will have a substantially different average boiling point than that of the feed mixture or any of its components, i.e., more than about 5° C. difference, to allow separation of at least a portion of the desorbent material from feed components in the extract and raffinate streams by simple fractional distillation, thereby permitting reuse of desorbent material in the process.

Finally, desorbent materials should be readily available and reasonable in cost. However, a suitable desorbent or desorbents for a particular separation with specific adsorbent are not always predictable. In the preferred isothermal, isobaric, liquid-phase operation of the process of this invention, I have found that desorbent materials comprising monocyclic alkyl-substituted aromatics, such as p- and m-diethylbenzene (p-DEB and m-DEB) or p-cymene, desorb the extract from the adsorbent and can be separated from the 3,5-DET product by distillation. Additionally, diluents for the desorbent can be used to modify the desorbent strength to achieve better separation, resolution and desorption rates. Examples of such dilution agents include normal paraffins, isoparaffins, ethers, and halogenated hydrocarbons.

Adsorption conditions will include a temperature range of from about 20° to 250° C. with about 60° to about 200° C. being more preferred and a pressure just sufficient to maintain liquid phase, which may be from about atmospheric to 600 psig. Desorption conditions will include the same range of temperatures and pressure as used for adsorption conditions.

Although both liquid and vapor phase operations can be used in many adsorptive separation processes, liquid-phase operation is preferred for this process because of the lower temperature requirements and because of higher yields of extract product that can be obtained with liquid-phase operation over those obtained with vapor-phase operation.

A dynamic testing apparatus is employed to test various adsorbents and desorbent material with a particular feed mixture to measure the adsorbent characteristics of adsorptive capacity and exchange rate. The apparatus consists of a helical adsorbent chamber of approximately 70-75 ml volume having inlet and outlet portions at opposite ends of the chamber. The chamber is contained within a temperature control means and, in addition, pressure control equipment is used to operate the chamber at a constant predetermined pressure. Quantitative and qualitative equipment, such as refractomers, polarimeters, chromatographs, etc., can be attached to the outlet line of the chamber and used to analyze, "on-stream", the effluent stream leaving the adsorbent chamber.

A pulse test, performed using this apparatus and the following general procedure, is used to determine data, e.g., selectivities, for various adsorbent systems. The adsorbent in the chamber is filled to equilibrium with a particular desorbent by passing the desorbent material through the adsorbent chamber. At a convenient time, a pulse of feed containing known concentrations of a tracer and of particular extract component or of a raffinate component, or both, normally diluted in desorbent material is injected for a duration of several minutes. Desorbent flow is resumed, and the tracer and the extract and raffinate components are eluted as in a liquid-solid chromatographic operations. The effluent can be analyzed by on-stream chromatographic equipment and traces of the envelopes of corresponding component peaks developed. Alternatively, effluent samples can be collected periodically and later analyzed separately by gas chromatography.

From information derived from the test, adsorbent performance can be rated in terms of void volume, retention volume for an extract or a raffinate component, and the rate of desorption of an extract component from the adsorbent and selectivity. Void volume is the nonselective volume of the adsorbent, which is expressed by the amount of desorbent pumped during the interval from the initial flow to the center of the peak envelope of the tracer. The net retention volume of an extract or a raffinate component may be characterized by the distance between the center of the peak envelope (gross retention volume) of the extract or raffinate component and the center of the peak envelope (void volume) of the tracer component or some other known reference point. It is expressed in terms of the volume in cubic centimeters of desorbent material pumped during this time interval, represented by the distance between the peak envelopes. The rate of exchange or desorption rate of an extract component with the desorbent material can generally be characterized by the width of the peak envelopes at half intensity. The narrower the peak width, the faster the desorption rate. The desorption rate can also be characterized by the distance between the center of the tracer peak envelope and the disappearance of an extract component which has just been desorbed. This distance is again the volume of desorbent material pumped during this time interval. Selectivity, $\beta$, is determined by the ratio of the net retention volumes (NRV) (gross retention volume (GRV) minus the void volume (GRV of the tracer)) of the more strongly adsorbed component to each of the other components.

The following non-limiting examples are presented to illustrate the process of the present invention and are not intended to unduly restrict the scope of the claims attached hereto.

EXAMPLE 1

The previously described pulse test apparatus was used to obtain data for this example. The liquid temperature was 165° C. and the flow was up the column at the rate of 1.26 ml/min. The feed stream comprised 2.0 ml pulses of a solution containing 1.5 ml of a mixture of diethyltoluene isomers, and 0.3 ml of n-hexane tracer and 1.0 ml of desorbent, 30% vol p-diethylbenzene in 70% (vol) isoctane. The mixture of DET isomers was approximately 43% (vol) 3,5-DET, 20% 2,5-DET, 23% 2,6-DET, 7% 2,3-DET, 2% 2,4-DET with trace amounts of other $C_{11}$ aromatics. The column was packed with clay bound K-X faujasite adsorbent of 20-50 mesh particle size. The 3,5-DET isomer was selectively adsorbed and recovered is the extract product.

The selectivity ($\beta$), as earlier described, was calculated from the trace of the peaks generated for the components. The results of this example are shown on the following Table I and FIG. 1.

TABLE 1

| Component | GRV (ml) | NRV (ml) | Beta($\beta$) |
|---|---|---|---|
| n-hexane | 41.6 | 0.0 | tracer |
| 3,5-DET | 76.4 | 34.8 | reference |
| 2,3-DET | 69.8 | 28.2 | 1.24 |
| 2,6-DET | 68.0 | 26.4 | 1.32 |
| 2,4-DET | 58.0 | 16.4 | 2.13 |
| 2,5-DET | 57.2 | 15.7 | 2.22 |

In general, the above data does show that the present invention provides a 3,5-diethyltoluene selective system, with adequate selectivities for the commercial use of the separation of the present invention.

EXAMPLE 2

Figure 2:
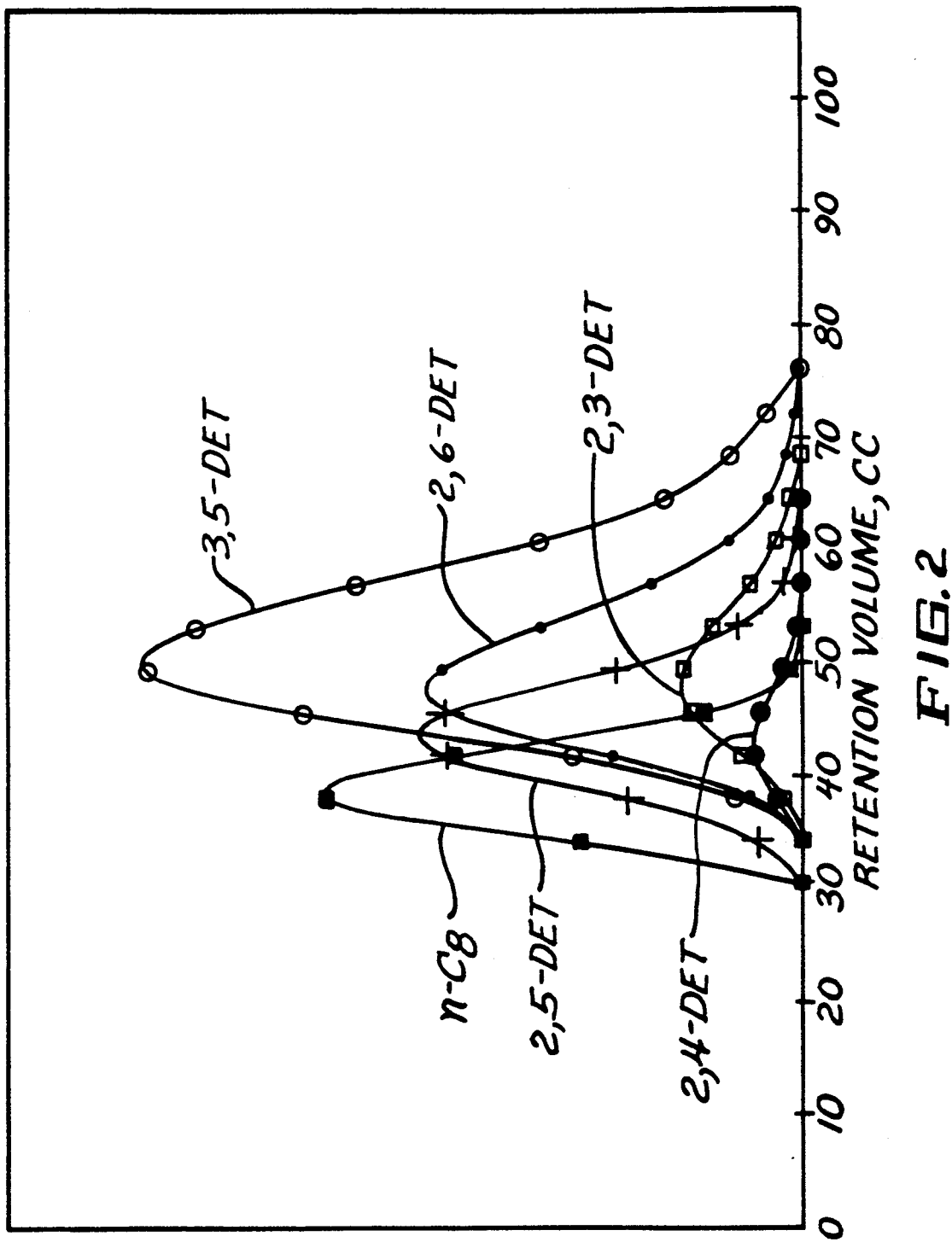
FIG. 2 is a chromatographic trace similar to FIG. 1, except that the desorbent is 100% p-cymene.

The previously described pulse test was also used to obtain data similar to that of Example 1, but using a desorbent other than exemplified above. In this case, the feed was 2 ml of a solution containing 1 ml of the same DET isomer mixture used in Example 1, 0.3 ml n-octane tracer, and 1 ml of desorbent. The desorbent was p-cymene. The column temperature was 145° C., flow rate up the column was 1.14 ml per min. The results of the pulse test are shown in FIG. 2 and Table 2 below.

TABLE 2

| Component | GRV (ml) | NRV (ml) | BETA($\beta$) |
|---|---|---|---|
| n-octane | 38.9 | 0.0 | tracer |
| 3,5-DET | 51.3 | 12.4 | reference |
| 2,4-DET | 43.2 | 4.2 | 2.93 |
| 2,3-DET | 49.0 | 10.1 | 1.23 |
| 2,6-DET | 48.8 | 9.8 | 1.26 |
| 2,5-DET | 43.9 | 4.9 | 2.51 |

EXAMPLE 3

Another pulse test was run using a 2 ml feed pulse of a solution containing 1.3 ml of the same DET isomer mixture of Example 1 and 0.7 ml of tracer, n-decane. After the feed pulse, the desorbent flow, which in this case was m-diethylbenzene (m-DEB), was resumed. Column flow was 1.3 ml per minute and the temperature was 200° C. Again, 3,5-DET was selectively adsorbed on the zeolite and desorbed with desorbent as shown in the following Table 4.

TABLE 4

| Component | GRV (ml) | NRV (ml) | BETA $\beta$ |
|---|---|---|---|
| n-C$_{10}$ | 38.5 | 0.0 | tracer |
| 3,5-DET | 67.9 | 29.3 | reference |
| 2,4-DET | 49.2 | 10.7 | 2.75 |
| 2,3-DET | 64.1 | 26.5 | 1.15 |
| 2,6-DET | 61.3 | 22.7 | 1.29 |
| 2,5-DET | 52.1 | 13.5 | 2.17 |

What is claimed is:

1. A process for separating 3,5-diethyltoluene from a feed mixture comprising 3,5-diethyltoluene and at least one isomer thereof, said process comprising contacting said mixture at adsorption conditions with an adsorbent comprising an X type zeolite, cation exchanged with a potassium cation thereby selectively adsorbing said 3,5-diethyltoluene, removing the remainder of said mixture from said adsorbent, and then recovering said 3,5-diethyltoluene by desorption at desorption conditions with a desorbent material comprising a monocyclic alkylsubstituted aromatic hydrocarbon having a boiling point differing by at least 5° C. from those of the components of the feed mixture.

2. The process of claim 1 wherein said adsorption and desorption conditions include a temperature within the range of from about 20° C. to about 200° C. and a pressure sufficient to maintain liquid phase.

3. The process of claim 1 wherein said process is effected with a simulated moving bed flow system.

4. The process of claim 1 wherein said process is effected with a static bed system.

5. The process of claim 1 wherein said hydrocarbon is selected from the group consisting of p- or m-diethylbenzene and p-cymene.

6. The process of claim 5 wherein said desorbent material additionally comprises a diluent.

* * * * *